US 8,205,612 B2

(12) United States Patent
Hickey et al.

(10) Patent No.: US 8,205,612 B2
(45) Date of Patent: Jun. 26, 2012

(54) DRY POWDER AEROSOL GENERATOR

(75) Inventors: Anthony J. Hickey, Chapel Hill, NC (US); Hugh D. C. Smyth, Albuquerque, NM (US); Martin J. Telko, Chapel Hill, NC (US)

(73) Assignee: The University of North Carolina at Chapel Hill, NC, Chapel Hill, NC (US)

( * ) Notice: Subject to any disclaimer, the term of this patent is extended or adjusted under 35 U.S.C. 154(b) by 885 days.

(21) Appl. No.: 11/724,147

(22) Filed: Mar. 14, 2007

(65) Prior Publication Data
US 2008/0223364 A1 Sep. 18, 2008

(51) Int. Cl.
*A61M 16/00* (2006.01)
*A01K 1/03* (2006.01)
(52) U.S. Cl. ......... 128/203.15; 128/200.24; 128/203.12; 119/420; 119/417
(58) Field of Classification Search ............. 128/203.12, 128/203.14, 203.15, 203.19, 203.22, 203.24, 128/205.26, 204.18; 119/420, 417, 418, 119/419, 651, 652, 665, 672
See application file for complete search history.

(56) References Cited

U.S. PATENT DOCUMENTS

| 1,559,750 | A | * | 11/1925 | Hemm et al. | 119/672 |
| 3,076,745 | A | * | 2/1963 | Eames | 119/174 |
| 4,462,244 | A | * | 7/1984 | Lee | 73/1.05 |
| 4,520,808 | A | * | 6/1985 | LaBauve | 128/200.14 |
| 4,622,852 | A | * | 11/1986 | James et al. | 73/865.6 |
| 4,721,060 | A | * | 1/1988 | Cannon et al. | 119/420 |
| 4,917,046 | A | * | 4/1990 | Spengler | 119/420 |
| 5,109,797 | A | * | 5/1992 | Briant et al. | 119/420 |
| 5,297,502 | A | * | 3/1994 | Jaeger | 119/420 |
| 5,379,777 | A | * | 1/1995 | Lomask | 600/529 |
| 5,680,996 | A | * | 10/1997 | Sadler, III | 241/57 |
| 6,140,659 | A | * | 10/2000 | Shizuka | 250/504 R |
| 7,234,269 | B2 | * | 6/2007 | Yonker et al. | 43/132.1 |

* cited by examiner

*Primary Examiner* — Justine Yu
*Assistant Examiner* — LaToya M. Louis
(74) *Attorney, Agent, or Firm* — Jenkins, Wilson, Taylor & Hunt, P.A.

(57) ABSTRACT

Dry powder aerosol generators and related methods are provided. The dry powder aerosol generator includes a dispersion chamber having an internal cavity therein capable of receiving a dry powdered drug. The dispersion chamber includes a dosing port defined therein that is in fluid communication with the internal cavity. A dosing chamber for receiving a test subject is attachable to the dosing port, such that, when an airflow is created within the internal cavity, any dry powdered drug contained therein may fluidize and travel into the dosing chamber to provide opportunity for inhalation of the dry powdered drug by a test subject contained within the dosing chamber.

24 Claims, 9 Drawing Sheets

Capreomycin Particles 10 mg Aerosolized in the dispersion chamber (Aero)

Fig. 9

DRY POWDER AEROSOL GENERATOR

TECHNICAL FIELD

The subject matter described herein relates to dry dose drug delivery systems and methods. More specifically, the present subject matter relates to a self-contained dry powder aerosol generator and methods of delivering drugs to the respiratory tracts of intended test subjects.

BACKGROUND

The delivery of drugs through dry powder aerosols to the respiratory tract of the intended patient or test subject is a common way to ensure the transfer of the drug into the system of the patient or test subject.

A variety of inhaler systems and methods exist for delivering dry powder to the respiratory tract of patients and/or test subjects. Metered dose inhalers deliver a metered dose of powdered drugs through inhalers that compress a canister or puncture a capsule. In such embodiments, the patient or test subject must inhale deeply in order to receive the required amount of dry powder to treat their ailment. In order for the patient or test subject to receive such dosage, the patient or test subject must make a conscious effort to inhale deeply at the appropriate moment in which the dry powder aerosol is ready to be delivered. However, for certain patients and test subjects, the ability to inhale deeply at the appropriate moment is not always controllable. For example, when delivering aerosols to certain test animals, a researcher cannot coax the animal or communicate with the animal being tested to make it inhale at the correct moment. Therefore, when testing animals with dry powder inhalation drugs, a low efficiency of deposition of the drug within the animal's respiratory tract often occurs. A similar problem occurs when trying to coax children to inhale at the proper moment.

When testing animals, direct insufflations may be used to deposit the drugs within the respiratory tract of the animal. However, this approach requires anesthesia and can cause untoward health problems in the animals and is not feasible for chronic treatment.

A variety of nebulizers and methods for using nebulizers have been employed to deliver drugs to the respiratory tracts of test subjects and patients. Such nebulizers do not require special breathing patterns. Nebulizers create a mist that is delivered in proximity to the mouth and nose of the patient or test subject. Nebulizers, however, require the use of a large amount of the drug in liquid form. The amount necessary to deliver an effective dosage to the patient or test subject is much larger than the amount deposited within the respiratory tract of the patient. A large majority of the drug being tested escapes into the surrounding environment. Therefore, much of the drug is wasted during a dosage session using a nebulizer. When testing drugs on small animals, the use of a nebulizer can waste large amounts of the drug being tested. These drugs are often times very expensive and time-consuming to make. Also, with experimental drugs, only small amounts of the drug may be available at any given time. Therefore, it is preferred that such nebulizing systems not be used for experimental drugs to conserve the drug for test purposes.

Therefore, a need exists for an improved delivery system of dry powdered aerosol drugs to test subjects that cannot consciously inhale deeply upon command to facilitate proper delivery of the drugs within the respiratory tract of the patient or test subject.

SUMMARY

According to certain aspects of the present subject matter, a dry powder aerosol generator is provided. The dry powder aerosol generator includes a dispersion chamber having sidewalls, a top and bottom. The dispersion chamber has an inner surface that defines an internal cavity within the chamber. The dispersion chamber also defines at least one dosing port in the sidewalls that is in communication with the internal cavity. The dry powder aerosol generator also includes a dosing chamber having a porthole end that is insertable in the at least one dosing port within the dispersion chamber. The dosing chamber defines an opening within the porthole end. The dry powder aerosol generator includes an impeller disposed within the internal cavity of the dispersion chamber. The impeller is capable of rotating at speeds that create an airflow that fluidizes a powdered drug introduced into the dispersion chamber. Further, the dry powder aerosol generator includes a controller in communication with the impeller for controlling the impeller.

According to another aspect of the present subject matter, a method for dosing an animal through the animal's respiratory tract is provided. The method includes providing a dry powder aerosol generator having a dispersion chamber with an internal cavity and at least one dosing port in communication with the internal cavity and at least one removable dosing chamber. The method also includes placing a test animal into the at least dosing chamber. The method also includes attaching the at least one dosing chamber to the at least one dosing port such that the at least one dosing chamber is in communication with the internal cavity. A dry powdered drug may be inserted into the internal cavity of the dispersion chamber. An airflow is created within the internal cavity of the dispersion chamber that fluidizes the dry powdered drug within the internal cavity so that the dry powdered drug migrates into the dosing chamber wherein the test animal may breathe in the dry powdered drug during its normal breathing process.

Some of the advantages of present subject matter have been stated hereinabove. Other advantages will become evident as the description proceeds when taken in connection with the accompanying drawings as best described herein below.

BRIEF DESCRIPTION OF THE DRAWINGS

A full enabling disclosure of the present subject matter including the best mode thereof to one of ordinary skill in the art is set forth more particularly in the remainder of this specification, including references to the accompanying figures in which.

DETAILED DESCRIPTION

Reference will now be made in detail to presently preferred embodiments of the present subject matter, one or more examples of which are shown in the figures. Each example is provided to explain the subject matter and not as a limitation of the subject matter. In fact, features illustrated or described as part of one embodiment can be used in another embodiment to yield still another embodiment. It is intended that the present invention covers such modifications and variations.

Figure 1:
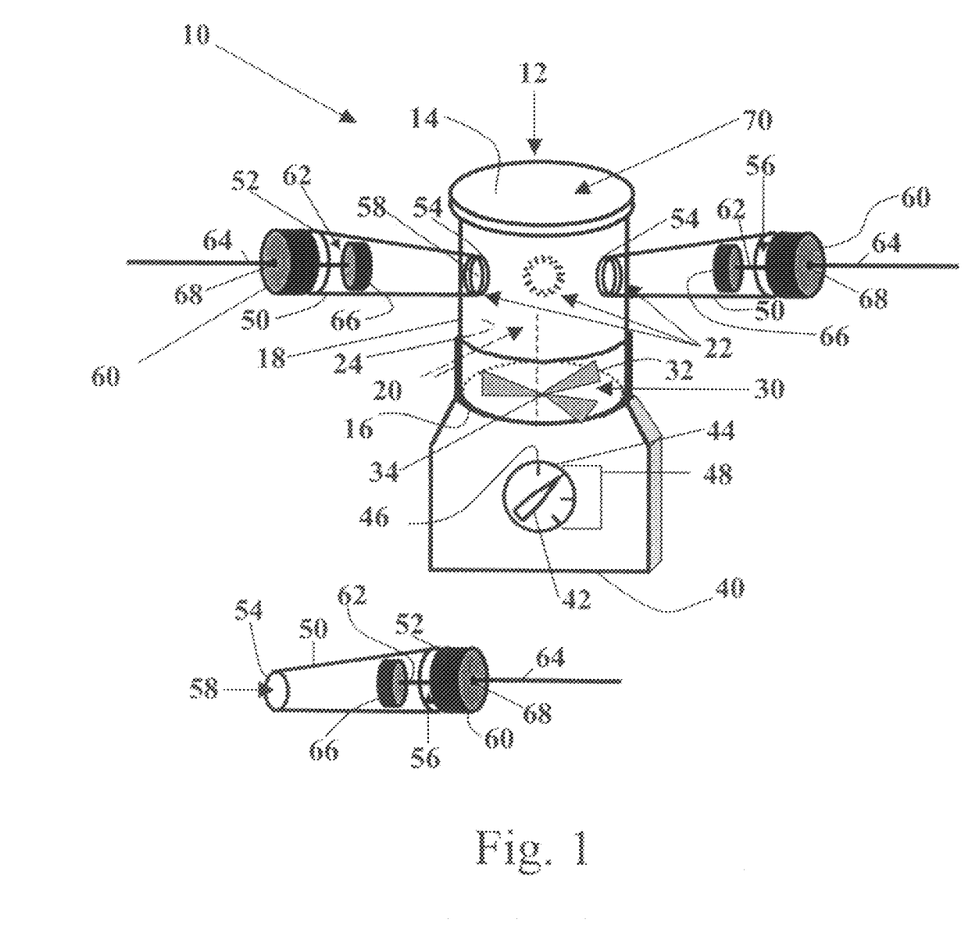
FIG. 1 illustrates a schematic perspective view of an embodiment of a dry powder aerosol generator according to the present subject matter.

FIG. 1 illustrates a schematic view of a dry powder aerosol generator, generally designated as 10. The dry powder aerosol generator 10 includes a dispersion chamber, generally designated as 12, which has a top 14, a bottom 16 and sidewalls 18. Sidewalls 18, top 14, and bottom 16 define an internal cavity, generally designated as 20. Dispersion chamber 12 can define dosing ports 22 that are in communication with internal cavity 20. An impeller 30 may reside within internal cavity 20 of dispersion chamber 12. Impeller 30 may reside near the bottom 16 of dispersion chamber 12. Impeller 30 may be secured to a motor (not shown) that rotates impeller 30 in order to create an airflow within dispersion chamber 12. Impeller 30 can have a plurality of blades 32 that can rotate around an axis 34 in order to create an airflow within dispersion chamber 12. For example, two impeller blades can form an impeller. In other embodiments as shown in FIG. 1, three or more blades may be used to form impeller 30. The size of impeller blades 32 are such that they may freely rotate within internal cavity 20 of dispersion chamber 12. The impeller can be centered along an axis of internal cavity 20. In such embodiments, the blades 32 may extend from axis 34 proximal to an inner surface 24 of dispersion chamber 12 which forms internal cavity 20. In such embodiments, the airflow created within the internal cavity 20 is generated from across a major portion of bottom 16 of dispersion chamber 12.

Impeller 30 may be rotated by a controller 40 which may include a motor (not shown) to which impeller 30 is attached. Controller 40 may permit a turning on and turning off of impeller 30 such that impeller 30 spins about axis 34 when the controller is at an ON position and comes to rest when the controller 40 is turned to an OFF position. Controller 40 may be a variable speed controller as shown in FIG. 1 that permits impeller 30 to rotate at different speeds, thereby creating different airflows and airflow velocities within dispersion chamber 12. For example, controller 40 may include a knob 42 which can be turned about a speed-setting dial 44. As shown in FIG. 1, speed-setting dial 44 can include an OFF position 46 and variable speed positions 48 at which impeller 30 may be rotated. Alternatively, controller 40 can be an infinite speed control that allows for incremental adjustment in speeds. Different speeds may be used with different drugs depending on variables such as particle size, adhesiveness of the particles, the cohesiveness of the particles, and the like.

Further, the type of animal to be tested may affect the speed at which the airflow is created. When a drug in powder form is introduced into dispersion chamber 12, impeller 30 is rotated causing the drug in powder form to become airborne such that the drug is fluidized and may reach the ports in which individual animals can inhale the drug during their normal breathing states.

Such a dry powder aerosol generator 10 can be particularly useful for large porous particles that have a density that is conducive for being suspended within the dispersion chamber 12 of the dry powder aerosol generator 10. Large porous particles have large geometric diameters, but due to their porosity and low density they have the mass and aerodynamic properties of much smaller particles. The large geometric diameter, however, reduces the interparticulate forces and the tendency of small particles to adhere to surfaces and to each other (aggregation). An example of such large porous particles is Dipalmitoylphosphatidylcholine ("DPPC"). DPPC is manufactured at Harvard University, located in Cambridge, Mass. DPPC can be mixed with drug compounds to form large porous particles that contain the drug compounds. Such large porous particles can be easily suspended in dispersion chamber 12.

Dry powder aerosol generator 10 can also include dosing chambers 50. Dosing chamber 50 may have an entrance end 52 and a porthole end 54. The dosing chamber 50 may include an opening 56 within entrance end 52 and an opening 58 within porthole end 54. The porthole end 54 of the dosing chamber 50 should fit snugly within dosing ports 22 within dispersion chamber 12. For example, the porthole end 54 may be equipped such that, when dosing chamber 50 and its porthole end 54 are placed within dosing port 22, an airtight seal may be created between porthole end 54 and the rim of dosing port 22 to prevent dry powdered drugs from escaping and external air from being introduced into the dispersion chamber 12. Alternatively, the connection between a dosing port 22 and a porthole end 54 of a dosing chamber 50 may not be airtight.

In embodiments in which small animals such as guinea pigs, rats, mice, or the like are tested, the opening 58 within porthole end 54 may be sized such that the fluidized drug in powder form may enter the dosing chamber allowing for the animal within the dosing chamber to receive an effective amount of the drug through normal breathing. The dosing chamber 50 may have a tapered shape. In particular, the internal cavity within the dosing chamber 50 may be tapered. Thereby, opening 56 of entrance end 52 may have a larger cross-section than opening 58 of porthole end 54. For example, dosing chamber 50 may have a truncated conical shape with entrance end 52 having a larger circular cross-section than porthole end 54. The internal cavity of dosing chamber 50 may be long and have a small diameter sized to direct the animal's head toward opening 58 of porthole end 54, while not providing enough room for the animal to move its head away from opening 58 of porthole end 54.

To help minimize any loss of drug in powder form, dosing chamber 50 may include a stopper 60 that is designed to fit in and close off opening 56 within entrance end 52. Stopper 60 may prevent the retreat of an animal being tested within dosing chamber 50 as well as prevent leakage of the powdered drug from the closed environment within dispersion chamber 12 and dosing chamber 50. Stopper 60 may include a prod 62 which extends through stopper 60 to prod the animal to be tested toward opening 58 within porthole end 54. Prod 62 may comprise a stem 64 and a head 66. Stem 64 of prod 62 may extend through an aperture 68 within stopper 60. The aperture 68 may be of a size that creates a frictional seal between the stem 64 and the stopper 60 that prevents, or at least minimizes, the loss of air and powdered drug from dosing chamber 50 through aperture 68. Head 66 of prod 62 resides within dosing chamber 50. Head 66 is firmly attached to stem 64 of prod 62. Stem 64 may be moved back and forth such that head 66 of prod 62 may be moved likewise within dosing chamber 50.

In use, an animal may be placed within dosing chamber 50 before the powdered drug is fluidized by impeller 30 within internal cavity 20 of dispersion chamber 12. Once the animal is placed within the dosing chamber, stopper 60 may be placed within opening 56 of entrance end 52 with head 66 residing within dosing chamber 50. Stem 64 of prod 62 may then be pushed forward to encourage the animal to move towards opening 58 of porthole end 54 so that when the controller 40 is turned on and impeller 30 rotates to fluidize the dry powdered drug, the animal will be in an optimal position to breathe the dry powdered drug into its respiratory tract.

As previously noted, dispersion chamber 12 includes inner surface 24 that defines internal cavity 20. Dispersion chamber 12 may have a cylindrical inner surface 24 such that the internal cavity 20 is cylindrical in shape. Such embodiments are conducive to having impellers 30 which extend close to inner surface 24, thereby creating an airflow from across the entire bottom 16 of dispersion chamber 12. However, other shapes may be used for the internal cavity. For example, the internal cavity may have a hexagonal cross-section, an elliptical cross-section, a rectangular or square cross-section, and the like in which multiple impellers are used. Further, the internal cavity may have a nonsymmetrical cross-section as well. However, minimizing the number of corners created within the chamber may be preferred to decrease the areas where airflow is slowed and particles would preferentially accumulate. Similarly, multiple impellers 30 may be used to provide the airflow that creates the fluidization of the dry powdered drug. For example, in an internal cavity having an elliptical cross-section, two impellers 30 can be used.

Dispersion chamber 12 may be made of wood, plastic, metal or the like. For example, dispersion chambers made of metal can help to dissipate the charge of the particles, thus reducing particle adhesion to inner surface 24 of dispersion chamber 12. The dispersion chamber can be made up of a composition of different materials. For example, the sidewalls may be comprised of metal while the top and bottom comprise a plastic material. Similarly, the dosing chambers 50 may be constructed of any material or combination of materials, such as wood, plastic or metal. For example, a clear plastic may be used to allow the researchers to monitor the animals during tests to ensure that they are in a proper position to permit breathing of the dry powdered drug during testing. The material used in the dispersion chambers and dosing chambers should provide a smooth surface either naturally or through proper treatment of the material to minimize the likelihood of the particles adhering to the surfaces within the chamber. In particular, inner surface 24 of dispersion chamber 12 may be smooth to minimize the attachment of drug particles to inner surface 24 of dispersion chamber 12. For example, inner surface 24 of dispersion chamber 12 may be finished and polished to reduce the amount of powdered drug deposited on and adhering to inner surface 24 of dispersion chamber 12.

Sidewalls 18 as discussed above may have at least one dosing port 22. However, multiple ports may be defined within sidewalls 18 of dispersion chamber 12. For example, three dosing ports 24 may be positioned along the sidewalls. In other embodiments, six ports may be positioned along the sidewalls of dispersion chamber 12. If multiple dosing ports 22 are defined within sidewalls 18 of dispersion chamber 12, then they may be placed at equal distance from one another. For example, if dispersion chamber 12 has a cylindrical outer surface, then three dosing ports 22 may be positioned at 120° from one another around the cylindrical sidewalls 18. Similarly, if six ports are used around cylindrical sidewalls 18, then the six dosing ports 22 may be positioned at 60° from one another around the sidewalls 18.

Top 14 of dispersion chamber 12 may be a lid, generally designated as 70, which is removable from dispersion chamber 12. Lid 70 can permit the introduction of the dry powder into the internal cavity 20 of dispersion chamber 12. Lid 70 may be lifted to allow the dry powdered drug to be poured in before impeller 30 is rotated. Lid 70 may be closed in order to keep dispersion chamber 12 self-contained and keep dry powder aerosol generator 10 as a relatively closed system. In some embodiments, the dry powdered drug may be introduced through other means such as a door, pluggable hole or the like.

The volume of the internal cavity 20 created by dispersion chamber 12 can be small and fixed. For example, the embodiment shown in FIG. 1 having a cylindrical internal cavity can have a height of about 20 cm and an internal diameter of about 10 cm. However, smaller or larger chambers can be expected to work as well and can depend on the size and nature of the test subjects and the amount of dry powder drug to be dispersed. Therefore, the exact dimensions can vary. The size range of the dry powder aerosol generator 10 can be such that it should provide a large enough volume for adequate fluidization without being significantly effected by the walls of the dispersion chamber, but small enough that the concentration of particles is sufficiently high for adequate exposure.

The dosing ports 22 may be positioned adjacent to top 14 of dispersion chamber 12. Such a construction can give high drug concentrations in small volumes with very little additional air added. When impellers 30 are rotated at sufficient speeds, a standing cloud is produced of the dry powdered drug which allows the fluidized drug to migrate toward the top and into the dosing chambers 50. For example, in the embodiment shown, the centers of the ports are positioned about 5 cm from the top of dispersion chamber 12. However, the location of the dosing ports along sidewalls 18 should be at the optimal level where the standing cloud of dry powder resides. Such location can be dependent on the volume size and volumetric shape of the internal cavity 20, the type of powdered drug used, and the force of the airflow created by the impeller 30.

In practice, if multiple dosing ports 22 are employed then one or multiple dosing chambers 50 may be used. If the total number of dosing chambers 50 used is less than the total number of dosing ports 22, then the dosing ports can be closed by a suitable stopper (not shown) which can be inserted into the dosing ports 22.

Figure 2:
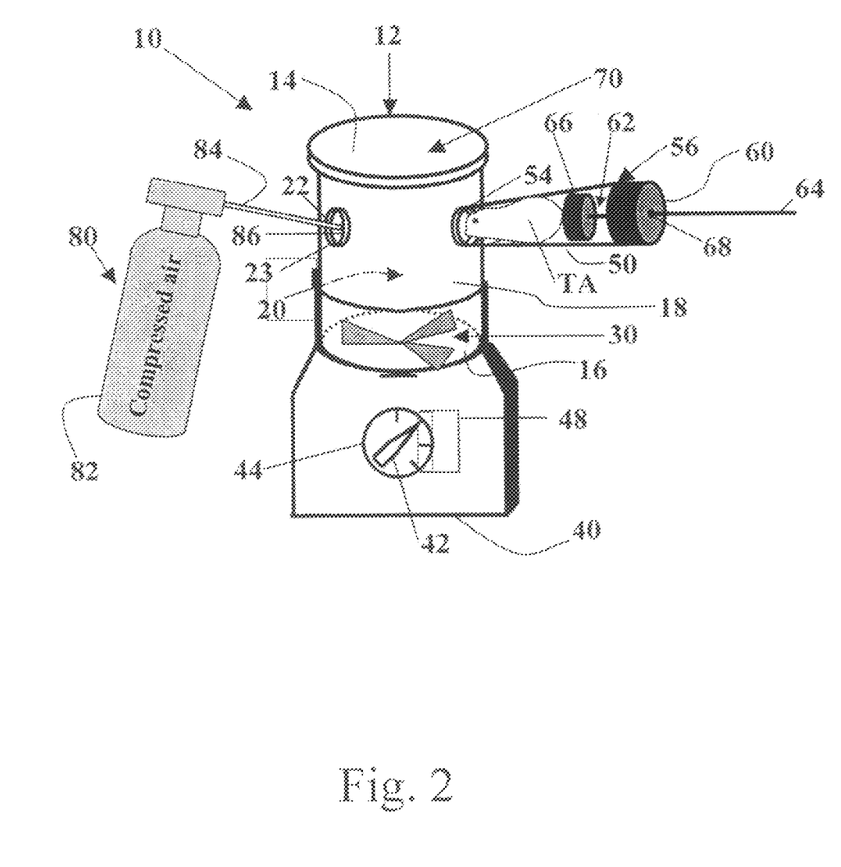
FIG. 2 illustrates a schematic perspective view of another embodiment of a dry powder aerosol generator according to the present subject matter with the dry powder aerosol generator in use.

FIG. 2 illustrates the dry powder aerosol generator, generally designated as 10, shown in FIG. 1. Dry powder aerosol generator 10 includes a dispersion chamber, generally designated as 12, having sidewalls 18, a top 14 and bottom 16 to define an internal cavity, generally designated as 20. The dispersion chamber 12 may have a cylindrical inner surface 24 which forms the internal cavity 20. An impeller 30 may be disposed within internal cavity 20. Impeller 30 may be controlled by a controller 40. Controller 40 may be a variable speed controller which allows an operator to control the rotation of impeller 30 through a control panel 44.

At least one dosing port 22 may be defined within sidewalls 18 of dispersion chamber 12 such that each dosing port 22 is in communication with internal cavity 20 of dispersion chamber 12. Dosing chamber 50 as described above may engage dosing port 22 such that a porthole end 54 of dosing chamber 50 is securable within dosing port 22.

As shown in FIG. 2, a test animal TA may be placed within an entrance end 52 of dosing chamber 50. Opening 56 of entrance end 52 may then be closed by a stopper 60 which has a prod 62 extending therethrough. The head portion 66 of prod 62 may be attached to a stem portion 64 that extends through stopper 60. The stem portion 64 may be pushed forward such that head portion 66 of prod 62 encourages the animal TA within dosing chamber 50 toward opening 58 of porthole end 54 of dosing chamber 50. A lid, generally designated as 70, which forms the top 14 of dispersion chamber 12 may be lifted to add a dry powdered drug into internal cavity 20 of dispersion chamber 12 before impeller 30 is turned on. Lid 70 may be placed back on dispersion chamber 12. Lid 70 can form an airtight seal to prevent escape of air and drug from internal cavity 20. However, in some embodiments, lid 70 may not form an airtight seal. Similarly, stopper 60 can form an airtight seal with dosing chamber 50 to prevent air and drug from escaping the closed system of dry powder aerosol generator 10. Again, in some embodiments, however, stopper 60 may not form an airtight seal.

Once knob 42 of speed-setting panel 44 of controller 40 is turned to a speed setting 48, impeller 30 begins to rotate thereby creating an airflow within internal cavity 20. This airflow lifts the particles of the dry powdered drug in dispersion chamber 12 to create a standing cloud within internal cavity 20 of dispersion chamber 12. Portions of the standing cloud migrate into dosing chamber 50 such that test animal TA can inhale the dry powdered drug into its respiratory tract during its normal breathing functions.

In order to keep the particles of the dry powdered drug circulating to maximize the amount of dry powdered drug within the standing cloud in the airflow created by impeller 30, strategic jets of air may be directed into internal cavity 20 of the dispersion chamber 12 so as to remove adhered powder from the inner surface 24 of dispersion chamber 12. These particles of the dry powdered drug are thereby re-circulated back into the airflow created by impeller 30. Such jets of air may come from a directable air supply, generally designated as 80. For example, the directable air supply 80 may be a canister 82 of compressed air having a long-nosed nozzle 84 which can be inserted into a nozzle port 86. Nozzle port 86 can be formed in sidewalls 18 and may have a diameter large enough to allow nozzle 84 of canister 82 to be directed in different directions within internal cavity 20 to allow short discrete jets of compressed air to be directed along sidewalls 18, the bottom 16 and lid 70 of dispersion chamber 12. Further, nozzle port 86 can be a size that minimizes loss of air and dry powdered drug therethrough when the nozzle 84 of the canister 82 is placed through the nozzle port 86.

In the embodiment shown in FIG. 2, nozzle port 86 may be disposed within a stopper 23 used to seal a dosing port 22 within sidewalls 18. Further, nozzle port 86 may be a stand-alone port that may be filled with a stopper when not in use. Multiple nozzle ports 86 may be placed around dispersion chamber 12 at different locations including the top 14, or lid 70, as well as along the expanse of the sidewalls 18. Further, nozzle ports 86 may also be placed along the bottom 16 of dispersion chamber 12.

Instead of using a nozzle port 86, a regular dosing port 22 which does not have a dosing chamber secured therein may be used to insert nozzle 84 of the canister 82 to supply the short and discrete jets of compressed air within internal cavity 20. The stopper, which may be placed within dosing port 22, can be removed during the time that nozzle 84 is inserted in dosing port 22. After the release of the short and discrete jets of compressed air, nozzle 84 can be removed and the stopper placed back in dosing port 22. In such embodiments, the stoppers within dosing port 22 help minimize the loss of air and powder from the internal cavity 22. However, when the nozzle is inserted to supply short and discrete jets of compressed air some air and dry powdered drug may escape from internal cavity 20 of dispersion chamber 12.

Canister 82 can be a commercial office-type compressed air canister that may be bought off the shelf at office supply stores. For example, the canister may be a canister of compressed air sold under the trademark DUST-OFF® and manufactured by Falcon Safety Products, Inc. of Branchburg, N.J.

The short and discrete jets of compressed air can introduce approximately 8 c.c. of air at a high linear velocity that easily detaches most of the adhered dry powdered drug from inner surface 24 within internal cavity 20. Such small introduction of air can change the pressure within dispersion chamber 12 if enough short, discrete jets are provided during the testing. However, in the embodiment shown in FIG. 2, nozzle port 86 can be such a size that it allows air to escape dispersion chamber 12. If such nozzle ports 86 are used, or when a dosing port 22 is used to insert nozzle 84 of canister 82, enough air escapes to equalize the pressure within dispersion chamber 12. Further, dispersion chamber 12 may not be absolutely airtight, allowing for the pressure within dispersion chamber 12 to remain at atmospheric pressure. In embodiments where nozzle ports 86 and dispersion chamber 12 are airtight, a pressure equalization valve may be used to equalize the pressure in the dispersion chamber 12 to the atmospheric pressure surrounding chamber 12.

Figure 3:
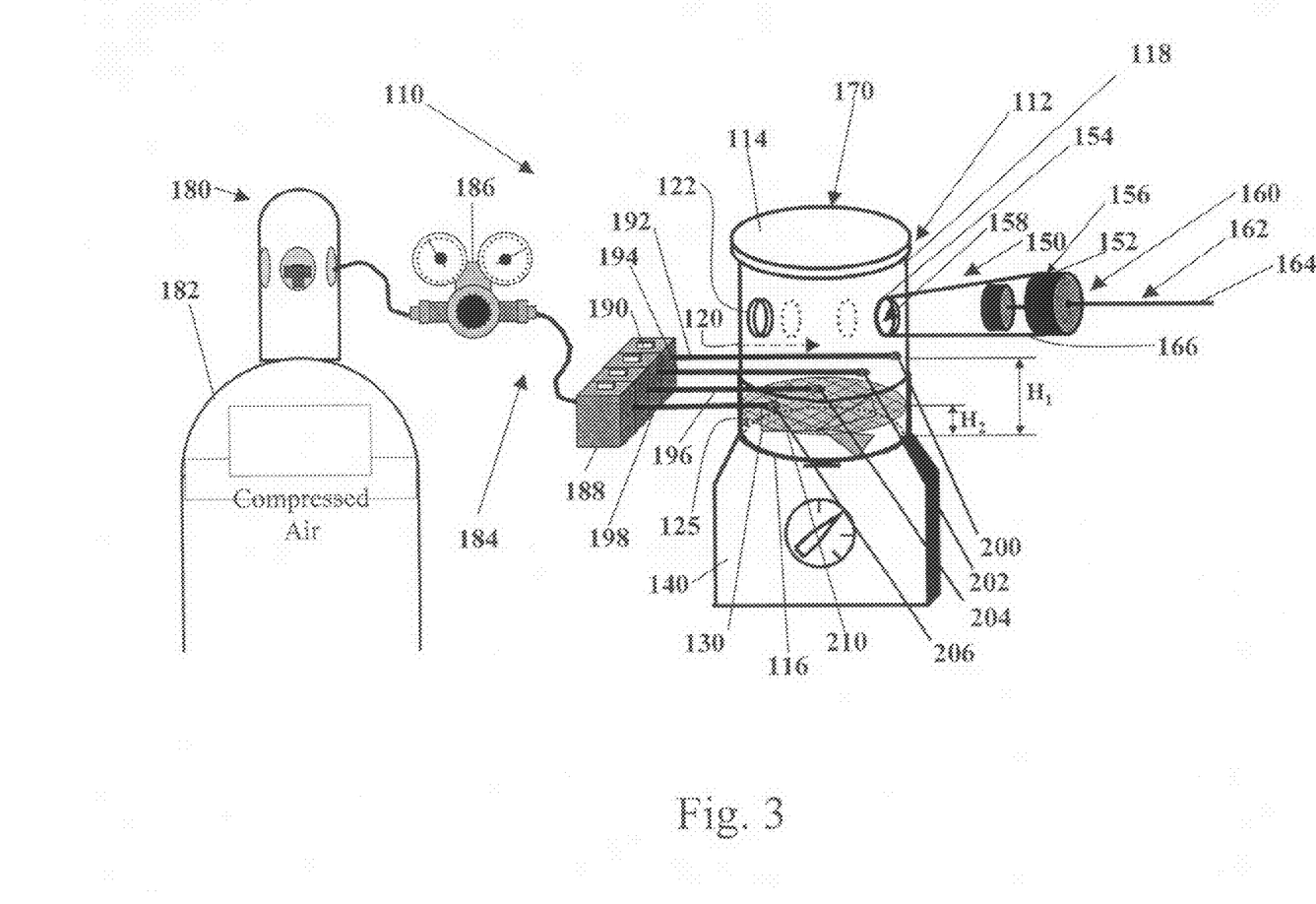
FIG. 3 illustrates a schematic perspective view of another embodiment of a dry powder aerosol generator according to the present subject matter.
Figure 4:
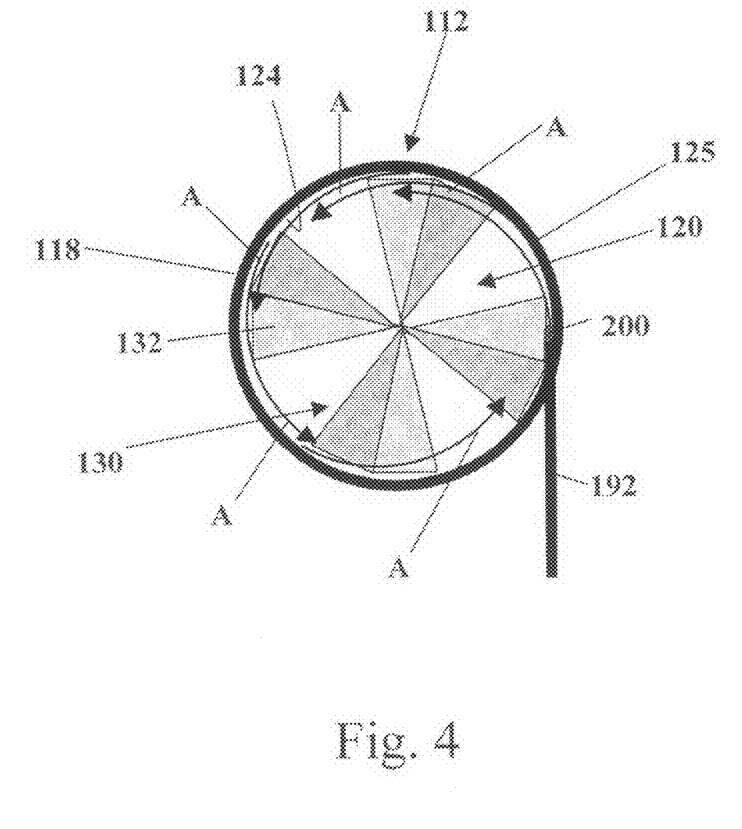
FIG. 4 illustrates a schematic cross-sectional view of the dry powder aerosol generator according to FIG. 3.

FIGS. 3 and 4 illustrate a further embodiment of a dry powder aerosol generator, generally designated as 110. Dry powder aerosol generator 110 includes a dispersion chamber, generally designated as 112, having a top 114, a bottom 116 and sidewalls 118 which define an internal cavity, generally designated as 120. Dosing ports 122 may be defined within sidewalls 118 such that dosing ports 122 are in communication with the internal cavity 120. An impeller 130 may be disposed within internal cavity 120 of dispersion chamber 112. Impeller 130 can be controlled by a controller 140. Controller 140 may be a variable speed controller as described above.

Dosing chambers, generally designated as 150, may be provided which are insertable into the plurality of dosing ports 122. Dosing chambers 150 provide a portion of the closed system in which an animal may be placed to be tested. The number of dosing chambers 150 may correspond to the number of dosing ports 122 disposed along sidewalls 118 of dispersion chamber 112. Dosing chamber 150 may include a porthole end 154 and an entrance end 152. Entrance end 152 may provide an opening in which to place an animal to be tested. Porthole end 154 may include an opening 158 that provides access to internal cavity 120 of dispersion chamber 112 once porthole end 154 of a dosing chamber 150 is placed within a dosing port 122. An airtight seal may be formed between dosing port 122 and porthole end 154 of dosing chamber 150. A stopper 160 may be placed within opening 156 of the entrance end 152 once an animal is placed within dosing chamber 150. Stopper 160 may include a prod 162 having a stem portion 164 and a head portion 166, which is used to prod the animal toward opening 158 of porthole end 150 of dosing chamber 150. The top 114 may be a lid, generally designated as 170, which can be lifted to allow introduction of the dry powdered drug into the internal chamber 120 of dispersion chamber 112. Impeller 130 may then be rotated at a speed that produces an airflow that suspends the dry powdered drug in a cloud which may migrate through dosing ports 122 and opening 158 of dosing chamber 150 to allow the test animal (not shown) disposed within dosing chamber 150 to receive the dry powdered drug into its respiratory tract through its normal breathing process.

The dry powder aerosol generator 110 may also include an air supply system, generally designated as 180, used to help keep dry powdered drug off the inner surface 125 of dispersion chamber 112. Air supply system 180 may include a compressed air source 182 and an air supply controller, generally designated as 184. The air supply controller may include a regulator 186 and a switch mechanism 188 which may direct air to different air lines 192, 194, 196, and 198. Switch mechanism 188 can include a plurality of buttons 190 with each button 190 controlling the flow of air through one of the air lines 192, 194, 196, and 198, respectively.

The dispersion chamber 112 may have at least one jet port defined within dispersion chamber 112. One or more jet ports 200, 202, 204, 206 can be defined within sidewalls 118 of dispersion chamber 112. These jet ports 200, 202, 204, 206 can be tangential to the circumference of inner surface 124 of dispersion chamber 112 to create an airflow around inner surface 124 of dispersion chamber 112 to blow off and re-suspend dry powdered drug that has been deposited on sidewalls 118.

As shown in FIG. 3, jet ports 200, 202, 204, 206 can be placed at different heights along sidewalls 118. For example, jet port 200 can be at a height $H_1$ as measured from the bottom 116 of dispersion chamber 112, while jet port 206 may be at a height $H_2$ that is less than height $H_1$ as measured from the bottom 116 of dispersion chamber 112. By providing multiple jet ports 200, 202, 204, 206 within sidewalls 118 that are located at different heights along sidewalls 118, short discrete jets of air may be supplied through air supply system 180 that blow off and re-suspend dry powdered drug that is deposited at different locations on inner surface 124 of dispersion chamber 112. These short, discrete jets along different heights and positions of sidewalls 118 thereby ensure that most of the dry powdered drug that has been deposited on inner surface 124 of dispersion chamber 112 is re-suspended within the airflow created by impeller 130. Summarily, in the embodiment shown in FIG. 3, lines 192, 194, 196, and 198 are attached to jet ports 200, 202, 204, 206, respectively. Each jet port 200, 202, 204, 206 is at a different height of dispersion chamber 112 and at a different position around inner surface 124 of dispersion chamber 112. The different heights and different positions at which jet ports can be defined in sidewalls 118 can be determined to optimize removal and re-suspension of dry powdered drug into the airflow created by impeller 130.

Switch mechanism 188 controls the supply of air through the respective air lines 192, 194, 196, and 198 to provide short, discrete jets of air to dispersion chamber 112 through the respective jet ports 200, 202, 204, 206. Switch mechanism 188 can be controlled manually through buttons 190. In some embodiments, switch mechanism 188 can be controlled through an automated process using a suitable computer, mini-computer, programmable logic controller, internal hardware or software or the like as a matter of design choice.

FIG. 4 illustrates an airflow pathway created by jet port 200 that is defined within dispersion chamber 112 through outer surface 125 and through inner surface 124 such that the jet port 200 is tangential to inner surface 124. Inner surface 124 has a cylindrical shape and jet port 200 is tangential to the circular cross-section of inner surface 124 along a plane in which jet port 200 resides. Therefore, when an air line 192 supplies a jet of air through jet port 200, air flow travels in a direction of arrows A shown in FIG. 4. Further, as the jet of air expands after exit from jet port 200, a greater surface area around inner surface 124 may be affected by the air, thereby re-suspending more dry powdered drug deposited therealong. The expansion of the jets of air along inner surface 124 can be taken into consideration when determining the optimum number of jet ports for sidewalls 118 and the optimum placement of the jet ports.

A screen 210 (see FIG. 3) may also be provided within internal cavity 120 of dispersion chamber 112. Screen 210 may be placed across the diameter of inner surface 124 and above impeller 130. Screen 210 can be made of a fine mesh or tight woven fabric which minimizes the amount of dry powdered drug that falls below impeller 130. Screen 210 can be constructed such that it prevents large particle powders having aerodynamic diameters in the micron range from passing through screen 210. At the same time, screen 210 allows an airflow generated from impellers 130 to pass through screen 210 to suspend the dry powder particles in a cloud that can enter dosing chamber 150 in which test animals reside. A screen size of approximately 100 micrometers may suffice.

Figure 5:
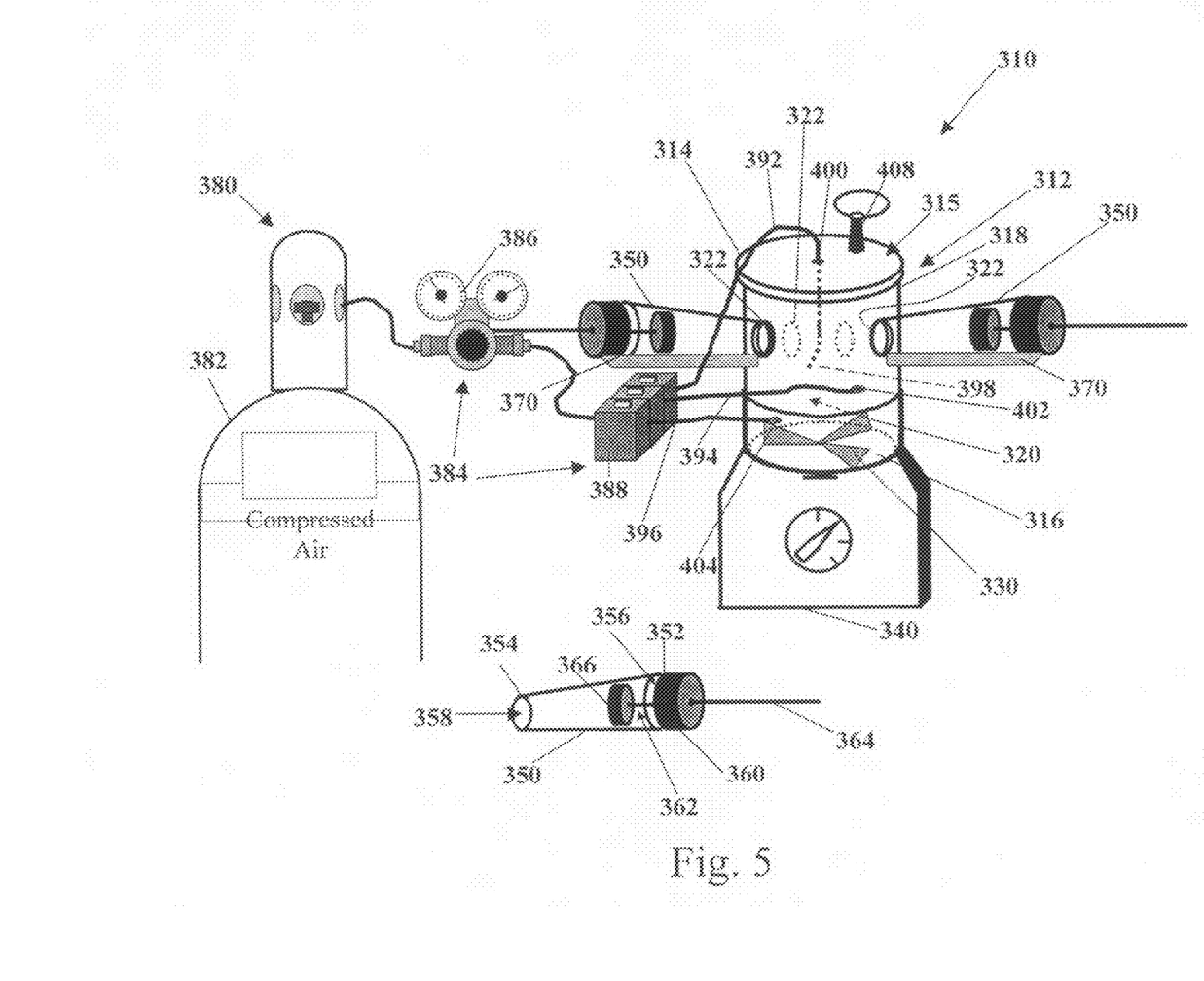
FIG. 5 illustrates a schematic perspective view of further embodiment of a dry powder aerosol generator according to the present subject matter.

FIG. 5 illustrates a further embodiment of a dry powder aerosol generator, generally designated as 310, similar to the embodiment shown in FIGS. 3 and 4. Dry powder aerosol generator 310 as described above can include a dispersion chamber, generally designated as 312, having a top 314, a bottom 316 and sidewalls 318 forming an internal cavity, generally designated as 320. As described above, the top 314 may be a lid, generally designated as 315, that allows introduction of the dry powdered drug into internal cavity 320 of dispersion chamber 312. Sidewalls 318 of dispersion chamber 312 can define a plurality of dosing ports 322. Impeller 330 may be controlled by controller 340 so that impeller 330 creates an airflow within dispersion chamber 312 to suspend the dry powdered drug. Dosing chambers 350 having an entrance end 352 and a porthole end 354 that define an opening 356 and an opening 358, respectively, provide passages in which to place animals to be tested. Porthole end 354 of a dosing chamber 350 with its opening 358 may be secured within a dosing port 322 defined within sidewalls 318 to allow a fluidized dry powdered drug to enter dosing chamber 350 and permit the test animal disposed therein (not shown) to receive the dry powdered drug within its respiratory tract through its normal breathing process. As described above, a stopper 360 may be provided for closing off opening 356 of entrance end 352. Stopper 360 can include a prod 362 for positioning the test animal near opening 358 of porthole end 354 and dosing port 322.

A support beam 370 (see FIG. 5) may be provided proximal to each dosing port 322 defined within sidewalls 318. Each support beam 370 is provided to help hold a corresponding dosing chamber 350 in its appropriate position within its corresponding dosing port 322. Support beams 370 allow larger animals to be placed in dosing chambers 350. Support beams 370 can provide the necessary support to hold corresponding dosing chambers 350 in the appropriate position for receiving the fluidized dry powdered drug to permit the dosing of the test animal contained therein.

Dry powder aerosol generator 310 may include an air supply system, generally designated as 380, that includes a compressed air source 382 and air supply controller, generally designated as 384. Air supply controller 384 may be configured in a similar manner as described above, with a regulator 386 and a switch mechanism 388. Further, the regulator 386 and the switch mechanism 388 can be a single solitary controller 384 used to control the supply of air to dispersion chamber 312. Switch mechanism 388 can be automated using a suitable computer, mini-computer, programmable logic controller, internal hardware or software, or the like as a matter of design choice. Such a switch mechanism can direct jets of air to different jet ports defined within dispersion chamber 312 at different times and at different intervals. For example, each jet port may be provided with a 0.1 second jet of compressed air at 30 p.s.i. at staggered intervals of 15 seconds.

In the embodiment shown in FIG. 5, dispersion chamber 312 includes a jet port 400 disposed at a center point within lid 315. Further, a jet port 402 can be defined in sidewalls 318 such that jet port 402 is tangential to the circumferential cross-section of the inner surface of dispersion chamber 312. Further, a jet port 404 can be defined within sidewalls 318 which directs air toward impeller 330 thereby helping to prevent buildup of dry powder particles on impeller 330 as well as underneath impeller 330 on the bottom of dispersion chamber 312.

Air jets supplied by the air supply system 380 may be sent through the different jet ports 400, 402, and 404. Airlines 392, 394, and 396, from air supply system 380 provide the jets of air through jet ports 400, 402, and 404 into internal cavity 320. Airline 392 is secured to jet port 400 within the center of lid 315 and can provide an air blast forcing the cloud downward towards dosing chambers 350 contained within dosing ports 322. Alternatively, as shown in FIG. 5, airline 392 may have a portion 398 (shown in dotted line) that extends through jet port 400 and into internal cavity 320. The portion 398 can undulate when the air is sent through air line 392. This undulation can cause the jet of air to be randomly directed in different directions. Further, the portion 398 can be rigid and be directed at a specific location in internal cavity 320.

Airline 394 supplies air to jet port 402 that provides jets of air within the internal cavity 320 as described in relation to FIGS. 3 and 4. Airline 396 provides jets of air to jet port 404, which directs the jets of air downward towards impeller 330 in the bottom 316 of dispersion chamber 312. Air supply controller 384 can selectively supply air to different jet ports at different times by providing short, discrete jets to facilitate and maintain the dry powdered drug within the airflow created by impeller 330. In an airtight closed system, the pressure within internal chamber 320 may be maintained at atmospheric pressure through a pressure equalization valve 408. Pressure equalization valve 408 can be secured to dispersion chamber 312 to allow the release of pressure that builds up due to the insertion of pressure through the air jets from air supply system 380. Pressure equalization valve 408, for example, may be located in the lid to allow the pressure to be equalized between the surrounding pressure outside dispersion chamber 312 and the pressure within dispersion chamber 312.

In Vitro Testing

Figure 6:
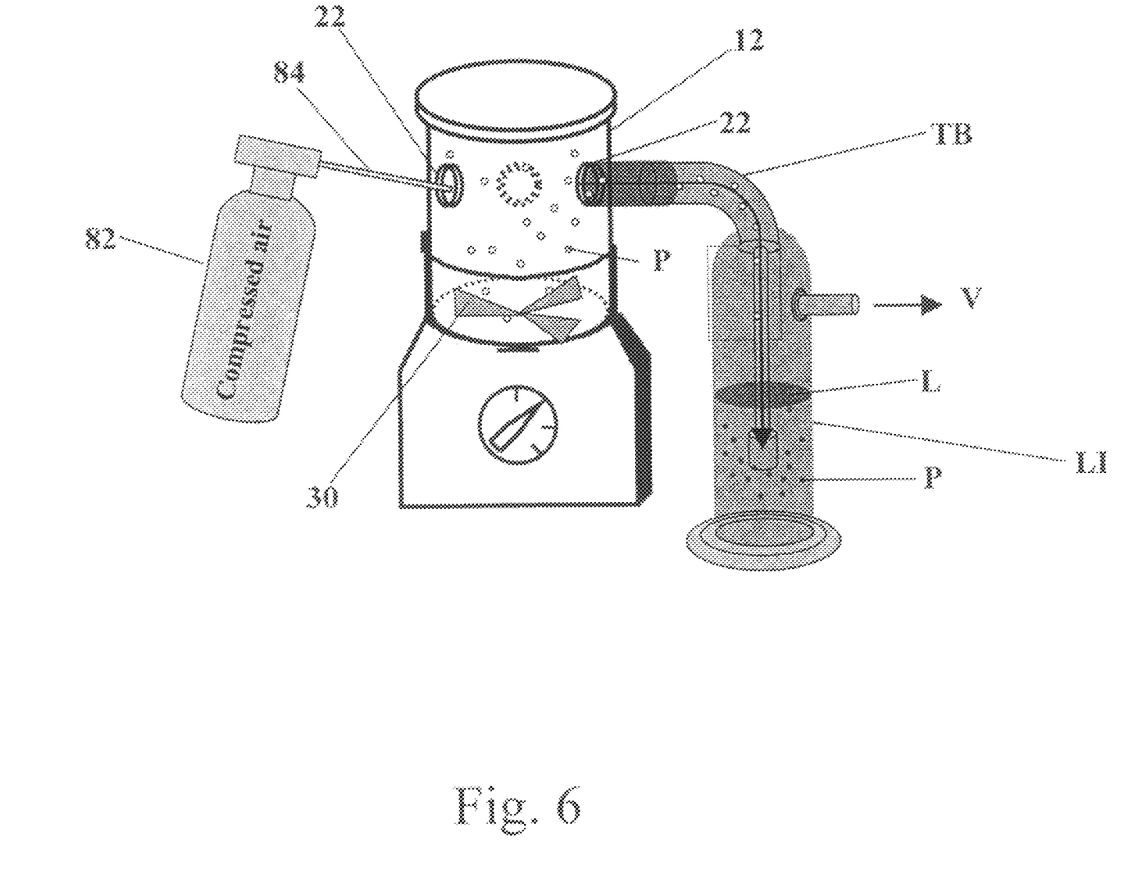
FIG. 6 illustrates a testing procedure of the dry powder aerosol generator as illustrated in FIGS. 1 and 2.

An embodiment similar to those illustrated in FIGS. 1 and 2 was tested to determine the delivery efficiency of the dry powdered aerosol generator for large porous particles. As shown in FIG. 6, a liquid impinger LI with tubing TB connected to a dosing port 22 of a dispersion chamber 12 of dry powder aerosol generator 10 was used to determine the amount of dry powdered particles P that were being received within a dosing chamber. Liquid impingers are commonly known particle collection devices in the art and will not be explained further in detail. Liquid impinger LI includes a vacuum V which operated at 2500 ml/min. as shown in FIG. 6. Compressed air from a canister 82 having a nozzle 84 was introduced through another dosing port 22 in short, discrete jets at regular intervals. The compressed air was used to remove dry particles P from the inner surface of dispersion chamber 12 and to re-suspend the particles P in the airflow created by impeller 30 during testing. The liquid impinger LI would catch particles P that pass through the dosing port to which it was connected and travel down the tubing TB and into the liquid L in the liquid impinger LI. The amount of particles P contained within the liquid L after testing was then measured.

Large porous particles containing capreomycin or capreomycin large porous particles ("CLPP") were tested using the liquid impinger LI. The CLPP was introduced into the chamber 12. Impeller 30 created a fluidization of the dry powdered drug. Short discrete jets of compressed air of approximately 8 c.c. were introduced every 15 seconds while suspending the CLPP over a 6 minute period. The amount of CLPP captured on the liquid of the liquid impinger was then measured. The test results showed a delivery efficiency of approximately of 8%, i.e., 8% of the drug loaded into chamber was recovered from the liquid in the liquid impinger.

Figure 7:
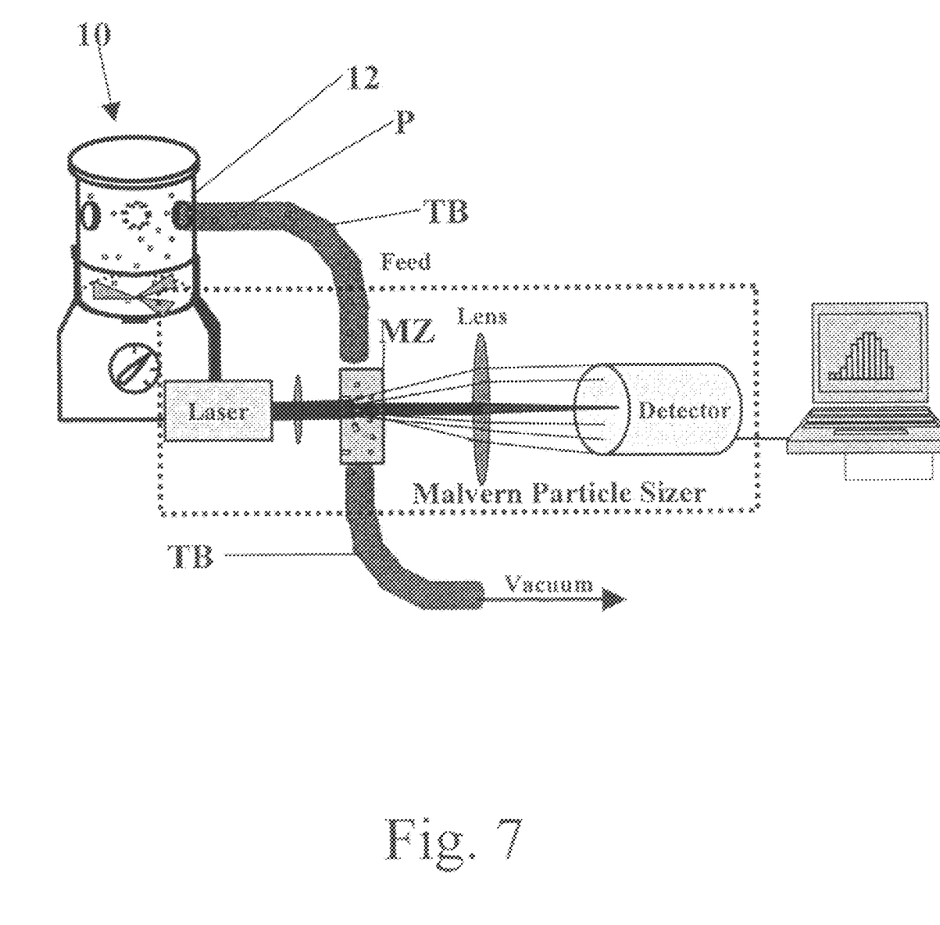
FIG. 7 illustrates a schematic view of the dry powdered aerosol generator of FIGS. 1 and 2 set up to test the dispersion of large particles within the chamber of the dry powder aerosol generator.

To determine how well a dry powder aerosol generator similar to those depicted in FIGS. 1 and 2 disperses particles, experiments were set up to characterize particles P that are delivered to the animal ports. Tubing TB was introduced into a dosing port of a chamber 12 of a dry powder aerosol generator, generally designated as 10, as shown in FIG. 7 and strictly maintained in the dosing port. Tubing TB was connected to a measuring zone compartment MZ which was intersected by the laser of a MALVERN sizer, manufactured by Malvern Instruments, Ltd., located in Worcestershire, United Kingdom. On the other side of the measuring zone compartment MZ, the tubing TB was continue through a liquid impinger and connected to a pump which drew air at approximately 30 liters per minute. The other dosing ports were closed off.

The first large particles tested were made from leucine and DPPC manufactured at Harvard University, located in Cambridge, Mass. These large particles have aerodynamic diameters in the micron range but smaller cohesive properties due to the increased size. Dispersion was assessed quantitatively.

Figure 8:
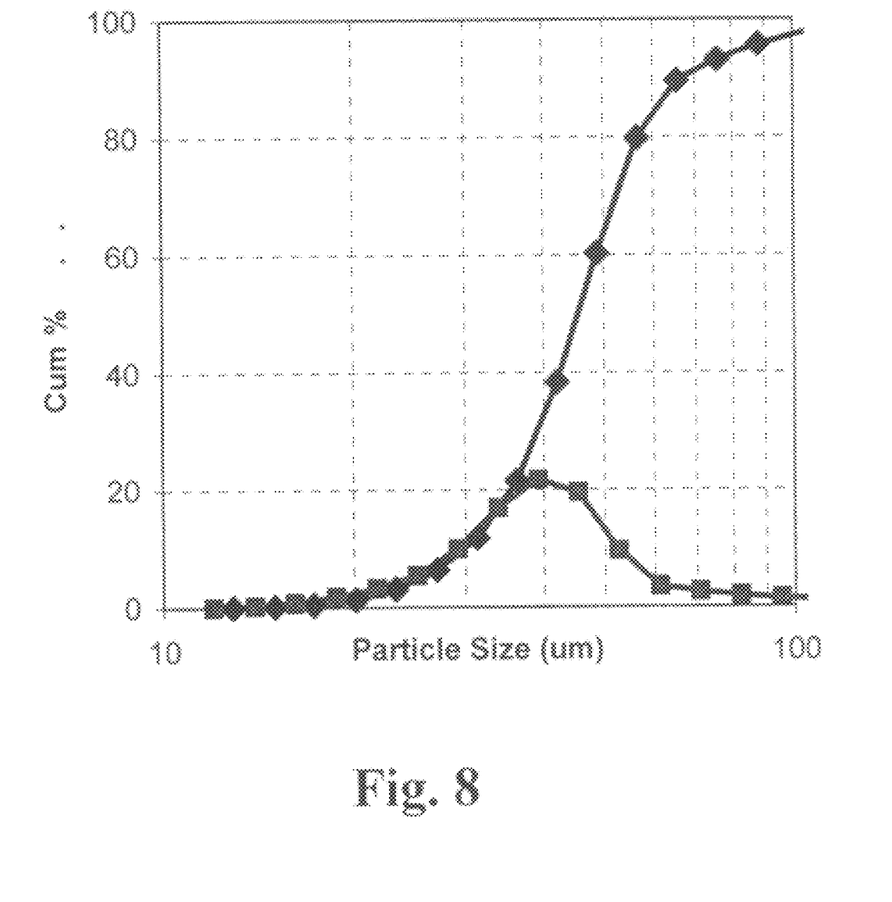
FIG. 8 illustrates a graph of particle size versus the amount of accumulation in both cumulative and interval distribution for the testing of the dry powder aerosol generator as shown in FIGS. 1 and 2.

Twenty milligrams of DPPC particles were loaded into the chamber, and the impeller was rotated. Measurements of dispersion were taken for several particles. Resulting particle diffraction data is shown in FIG. 8. The dark diamonds show an accumulative geometric particle size distribution of luceine: DPPC large pore particles sampled from the animal ports after suspension inside the dry powder aerosol generator 10. The light square points illustrate interval geometric particle size distribution. FIG. 8 shows that the dry powder aerosol generator successfully suspended particles and made them available for inhalation to the animals. As shown in FIG. 8, the dry powder aerosol generator fluidizes and disperses the particles sufficiently so that particles are delivered into the ports and are available for inhalation by the resident animal.

In Vivo Testing

Once a dispersability testing was conducted and delivery efficiency was determined using a liquid impinger, in vivo experiments were conducted to assess the actual amount deposited in the lung of an animal. The tests were performed in a dry powder aerosol generator similar to those described in FIGS. 1 and 2. Two healthy animals, in the form of guinea pigs, were prepared for pharmacokinetics studies. The guinea pigs were placed in the dry powdered dosing chamber, as shown in FIG. 2, and dosed with dispersed capreomycin ("CLPP"). About 30 mg of CLPP were loaded into the chamber every four minutes for 32 minutes for a total of about 240 mg. It was estimated that each guinea pig inhaled about 10 mg of the CLPP based on tidal volume, length of exposure, and a delivery efficiency of approximately 8%. Particles dispersion was aided by compressed air as described above in the In vitro testing.

Figure 9:
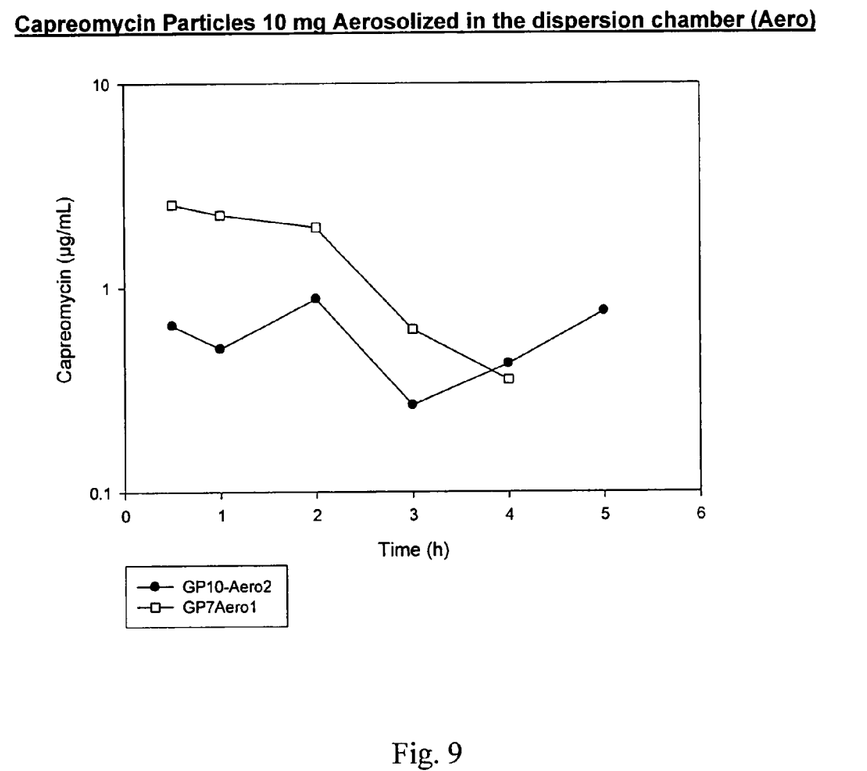
FIG. 9 illustrates a graph of the comparison of average plasma concentration versus time curves after administration of capreomycin particles using a dry powder aerosol generator as illustrated in FIGS. 1 and 2.

After dosing, blood samples were collected for predetermined periods of time (PK Studies). The plasma was separated from the blood and analyzed for CLPP concentrations by high performance liquid chromatography ("HPLC"). Capreomycin plasma concentrations versus time curves for these two guinea pigs are shown in FIG. 9. Capreomycin plasma concentration curves of animals receiving aerosolize particles were different from each other. For Animal 1 ("Aero 1") plasma concentrations were between approximately 5 µg/ml of plasma and about 0.5 µg/ml of the plasma over a 4 hour period. In contrast, the plasma concentration versus time curves for Animal 2 ("Aero 2") produced a capreomycin level between about 1 µg/ml of plasma and about 0.5 µg/ml of plasma over a 5 hour period. Exposure, measured as areas of the plasma concentration-time curve ("AUC"), was calculated by nonlinear methods for Aero 1 and Aero 2 and the fraction delivered by the aerosol was calculated. This delivery fraction equaled about 34.7% and 13.8% for Aero 1 and Aero 2, respectively.

In order to calculate the actual dose delivery to each animal, the following equation was employed:

$$F = \frac{AUC_{aero}}{AUC_{iv}} \times \frac{Dose_{iv}}{Dose_{aero}}. \quad \text{EQ (1)}$$

Where F is the absolute bioavailability, $AUC_{LUNG}$ and $D_{LUNG}$ are the area under the curve and dose, respectively, for drug administration through the lung. $AUC_{IV}$ and $D_{IV}$ are areas under the curve and dose, respectively, of drug administered intravenously. From internal PK Studies performed, it is known that F equals 0.54 for capreomycin particles administered through the lungs, $AUC_{IV}$ equals 48.47 µgh/ml, and $D_{IV}$ equals 20 mg/kg.

Dosage received depends on the body weight of the animal being tested as well. This is shown through the equation provided below:

$$\text{Dosage received} = (GP \text{ body weight})(D_{LUNG}) \quad \text{EQ (2)}$$

Body weights of Aero1 and Aero2 guinea pigs were 606 g and 750 g, respectively. Thus, the actual dose received by Aero1 was 2.74 mg and by Aero 2 was 1.33 mg. Finally, the efficiency of the delivery expressed as a fraction of the dosage received was calculated by the following equation:

$$\text{\% Efficiency of delivery} = [(\text{dose received}) \div (\text{dose delivered})] \times 100 \quad \text{EQ (3)}$$

If the total dose loaded into the chamber was 100 mg of capreomycin particles for three animals, the percent of efficiency of delivery of Aero 1 was approximately 8.22% and for Aero 2 was 3.99%.

The embodiments of the present disclosure shown in the drawings and described above are exemplary of numerous embodiments that can be made within the scope of the appending claims. It is contemplated that the configurations of the dry powdered aerosol generator and the methods of making a dry powdered aerosol comprising numerous configurations other than those specifically disclosed. Thus, it is applicants' intention that the scope of the patent issuing herefrom will only be limited by the scope of the appending claims.

What is claimed:

1. A dry powder aerosol generator for fluidizing a powdered drug and comprising:
   (a) a dispersion chamber having at least one sidewall and a top and a bottom, the dispersion chamber having an inner surface that defines an internal cavity within the chamber and wherein the dispersion chamber prevents airflow communication between inside and outside of the dispersion chamber, the dispersion chamber also having at least one dosing port in the at least one sidewall, the at least one dosing port being in communication with the internal cavity;
   (b) a dosing chamber having a porthole end that is insertable in the at least one dosing port of the dispersion chamber, the dosing chamber defining an opening within the porthole end;
   (c) an impeller enclosed within the internal cavity of the dispersion chamber configured to create an airflow within the dispersion chamber to produce a standing cloud of powdered drug after introduction of the powdered drug into the dispersion chamber; and
   (d) a controller in operative communication with the impeller for controlling the rotation of the impeller.

2. A dry powder aerosol generator as in claim 1, wherein the dispersion chamber defines a cylindrical inner surface.

3. A dry powder aerosol generator as in claim 2, wherein the impeller comprises a set of blades that extend from the center of the dispersion chamber outward proximal to the at least one sidewall of the dispersion chamber so that the impeller extends across a majority of a bottom of the inner surface of the dispersion chamber.

4. A dry powder aerosol generator as in claim 1, wherein the at least one dosing port comprises three dosing ports.

5. A dry powder aerosol generator as in claim 1, wherein the at least one dosing port comprises six dosing ports.

6. A dry powder aerosol generator as in claim 1, wherein the top of the dispersion chamber comprises a lid that is removable from the dispersion chamber.

7. A dry powder aerosol generator as in claim 1, wherein the dispersion chamber has a smooth inner surface.

8. A dry powder aerosol generator as in claim 1 wherein the at least one sidewall of the dispersion chamber comprise a metal.

9. A dry powder aerosol generator as in claim 1, wherein the dosing chamber further comprises an entrance end opposite the porthole end, the entrance end defining an opening therein.

10. A dry powder aerosol generator as in claim 9, wherein the dosing chamber has a tapered shape with the opening of the porthole end having a smaller cross-section than a cross-section of the opening of the entrance end.

11. A dry powder aerosol generator as in claim 10, wherein the dosing chamber has a conical shape with the opening of porthole end having a smaller circular cross-section than a circular cross-section of the entrance end.

12. A dry powder aerosol generator as in claim 9, further comprising a stopper for closing the opening within the entrance end of the dosing chamber.

13. A dry powder aerosol generator as in claim 12, wherein the stopper includes a prod having a stem portion and a head portion, the stem portion of the prod extending through the stopper with the head portion attached to the stem portion and capable of residing within the dosing chamber, the prod being movable within the dosing chamber.

14. A dry powder aerosol generator as in claim 1, wherein the controller comprises a motor.

15. A dry powder aerosol generator as in claim 14, wherein the controller comprises a variable speed controller.

16. A dry powder aerosol generator as in claim 1, further comprising a screen disposed above the impeller.

17. A dry powder aerosol generator as in claim 1, further comprising a dosing chamber support extending outward from an outer surface of the dispersion chamber proximal to the at least one dosing port.

18. A method for dosing an animal through the animal's respiratory tract, the method comprising:
    (a) providing a dry powder aerosol generator having at least one removable dosing chamber and a dispersion chamber with an internal cavity wherein the dispersion chamber prevents airflow communication between inside and outside of the dispersion chamber, and at least one dosing port in communication with the internal cavity;
    (b) placing a test animal into the at least dosing chamber;
    (c) attaching the at least one dosing chamber to the at least one dosing port such that the at least one dosing chamber is in communication with the internal cavity;
    (d) inserting a dry powdered drug into the internal cavity of the dispersion chamber; and
    (e) creating an airflow within the dispersion chamber with an impeller enclosed within the internal cavity that fluidizes the dry powdered drug within the internal cavity to produce a standing cloud of the powdered drug proximal to the at least one dosing port so that the dry powdered drug migrates into the at least one dosing chamber wherein the test animal may breathe in the dry powdered drug during its normal breathing process.

19. A method as in claim 18, wherein the at least one dosing port comprises a plurality of dosing ports and the at least one dosing chamber comprises a plurality of dosing chambers with each dosing port of the plurality of dosing ports being capable of receiving one dosing chamber of the plurality of dosing chambers.

20. A method as in claim 18, wherein the step of creating an airflow within the internal cavity of the dispersion chamber further comprises spinning the impeller within the internal cavity to create the airflow.

21. A method as in claim 18, further comprising stopping up an entrance end of the at least one dosing chamber to prevent escape of the test animal and minimize loss of the dry powdered drug.

22. A method as in claim 21, further comprising prodding the test animal toward an end of the dosing chamber proximal to the at least one dosing port to which the dosing chamber is attached.

23. A dry powder aerosol generator for fluidizing a powdered drug and comprising:
    (a) a dispersion chamber having an inner surface that defines an internal cavity within the chamber and wherein the dispersion chamber prevents airflow communication between inside and outside of the dispersion chamber, the dispersion chamber also having at least one dosing port defined therein, the at least one dosing port being in communication with the internal cavity;
    (b) a dosing chamber having a porthole end that is insertable in the at least one dosing port of the dispersion chamber, the dosing chamber defining an opening within the porthole end;
    (c) an impeller enclosed within the internal cavity of the dispersion chamber configured to create an airflow within the dispersion chamber to produce a standing cloud of powdered drug after introduction of the powdered drug into the dispersion chamber; and
    (d) a controller in operative communication with the impeller for controlling the rotation of the impeller.

24. A dry powder aerosol generator as in claim 23, wherein the impeller is disposed within the internal cavity of the dispersion chamber near a bottom of the inner surface of the dispersion chamber and the impeller extends across a large portion of the bottom of the inner surface so that the airflow created within the internal cavity is generated from across a major portion of the bottom.

* * * * *